(12) United States Patent
Staats

(10) Patent No.: US 7,060,227 B2
(45) Date of Patent: Jun. 13, 2006

(54) MICROFLUIDIC DEVICES WITH RAISED WALLS

(76) Inventor: Sau Lan Tang Staats, 609 Ramsey Rd., Hockessin, DE (US) 19707

( * ) Notice: Subject to any disclaimer, the term of this patent is extended or adjusted under 35 U.S.C. 154(b) by 618 days.

(21) Appl. No.: 10/213,202

(22) Filed: Aug. 5, 2002

(65) Prior Publication Data

US 2003/0026740 A1 Feb. 6, 2003

Related U.S. Application Data

(60) Provisional application No. 60/310,337, filed on Aug. 6, 2001, provisional application No. 60/378,881, filed on May 8, 2002.

(51) Int. Cl.
*B81B 1/00* (2006.01)
(52) U.S. Cl. ................... 422/100; 422/68.1
(58) Field of Classification Search ........... 438/42; 422/68.1, 100, 920, 946, 947, 924
See application file for complete search history.

(56) References Cited

U.S. PATENT DOCUMENTS

| 4,756,884 A | 7/1988 | Hillman et al. |
| 5,486,335 A | 1/1996 | Wilding et al. |
| 5,872,010 A * | 2/1999 | Karger et al. ............... 436/173 |
| 5,900,130 A | 5/1999 | Benvegnu et al. |
| 5,932,315 A * | 8/1999 | Lum et al. .................. 428/172 |
| 5,992,820 A | 11/1999 | Fare et al. |
| 6,210,986 B1 * | 4/2001 | Arnold et al. ................. 438/42 |
| 6,478,238 B1 * | 11/2002 | Wachs et al. ............... 239/338 |
| 2002/0000516 A1 * | 1/2002 | Schultz et al. ............. 250/288 |
| 2004/0053403 A1 * | 3/2004 | Jedrzejewski et al. ... 435/287.2 |
| 2004/0115838 A1 * | 6/2004 | Quake et al. ............... 436/538 |
| 2005/0000900 A1 * | 1/2005 | Huang et al. ............... 210/656 |
| 2005/0009101 A1 * | 1/2005 | Blackburn .................. 435/7.1 |

* cited by examiner

Primary Examiner—Jill Warden
Assistant Examiner—Paul S. Hyun
(74) *Attorney, Agent, or Firm*—Darby & Darby

(57) ABSTRACT

A microfluidic device is provided and comprises a device that is assembled from segments of microfluidic features using built-in alignment features, such as the raised walls of the channels or protrusion/recess pairs to comprise channels, nozzles, optical detectors, distillation columns, etc., to form a device for a specific application, such as an electrospray-mass spectrometer interface. Some of the segments can be of standard dimensions with standard alignment features so that the user may assemble microfluidic devices for specific applications using standard prefabricated segments as part thereof.

19 Claims, 10 Drawing Sheets

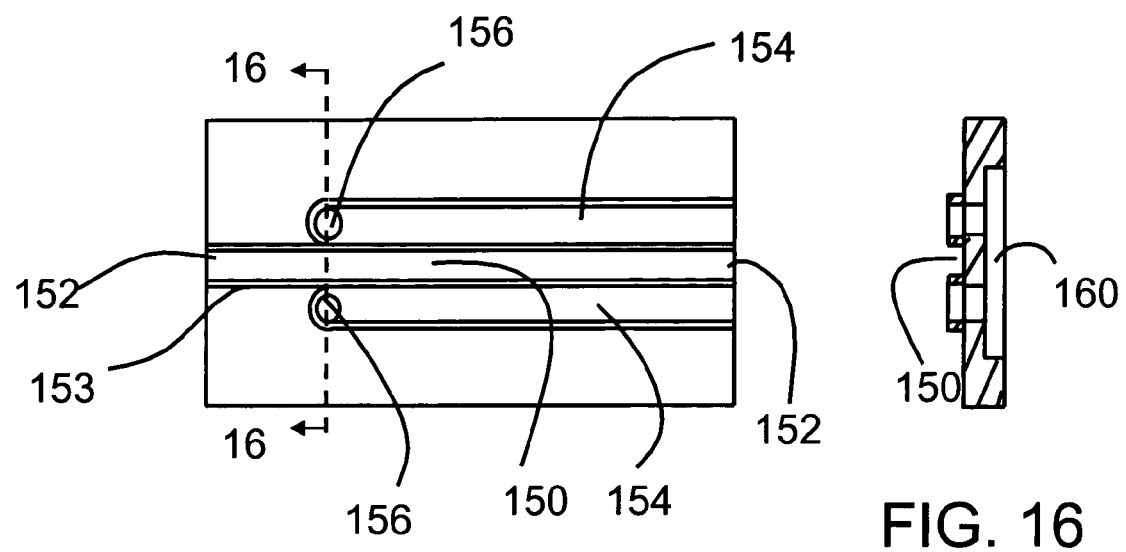
FIG. 14
FIG. 16
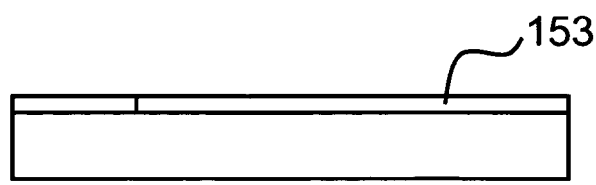
FIG. 15

MICROFLUIDIC DEVICES WITH RAISED WALLS

CROSS REFERENCE TO RELATED APPLICATION

This application claims the priority of U.S. Provisional Application No. 60/310,337, filed Aug. 6, 2001, and U.S. Provisional Application No. 60/378,881, filed May 8, 2002, which are both hereby incorporated by reference in their entirety.

Technical Field

This invention relates to microfluidic devices. These devices form layered, three-dimensional structures and provide a liquid handling interface with external devices. These microfluidic devices are suitable for operations designed for lab-on-a-chip functions.

Background

A microfluidic, or lab-on-a-chip (LOC), device is a planar device, one surface of which contains some of the following microfluidic features: interconnecting channels, reservoirs, valves, flow switches, etc., which are fabricated using semiconductor microfabrication technology. This surface is sealed by another planar surface so that liquid moves in enclosed spaces except where samples are injected from the outside world by means of syringes or micropipettes, etc. The microfluidic features are designed to carry out complex laboratory functions such as DNA sequencing. Analytical measurements are also carried out directly on the device. The first of such devices disclosed in the patent literature was made of silicon as disclosed by Pace in U.S. Pat. No. 4,908,112.

Microfluidic devices are considered the enabling technology for low cost, high versatility, operations, many of which find great utility in biotech and pharmaceutical industries. Applications of planar microfabricated devices primarily include using electroosmotic, electrokinetic, and/or pressure-driven motions of liquids and particles for fluid transport are well known.

A common means of injecting samples into the enclosed fluid channels for analytical operations such as capillary electrophoresis (CE) is intersecting channels connecting the sample reservoirs to the main fluid separation channels. The intersecting channels can be in the form of a 'T' or a cross. A sample to be injected from a sample reservoir to the fluidic channel by an electrokinetically driven operation requires a voltage (Vs) to be applied to the sample reservoir or well. Another voltage or electrical ground (Vsw) is applied to the sample waste reservoir, typically situated beyond the junction point of the sample injection channel and the main fluidic channel. A stream of the sample is electrokinetically transported from the sample reservoir toward the waste reservoir, intersecting the main fluidic channel en route. An injection plug into the main fluidic channel is formed when the voltage difference Vs−Vsw is reduced or eliminated, thus stopping the stream, and another voltage, Vb, is applied to the run buffer well and, a voltage Vbw the buffer waste well. In this mode of sample injection, a sample well, a buffer well and at least 1 waste well are needed. Even when only several nanoliter of sample is needed for the separation experiment, a much larger quantity of sample must be placed in the sample well to establish the flow toward the main microfluidic channel, which may be the CE separation channel.

If automatic sample filling of the device is needed as in the case of 96-channel CE devices for high-throughput applications, a coupler can be used to couple the sample from an external vessel into the sample well on the device via a capillary. Once the sample is deposited into the sample well, the same injection procedure as described above is carried out.

In liquid phase applications, especially in capillary electrophoresis, the channel widths used by those skilled in the art are generally uniform in width with the most common width at about 100 µm or smaller.

The prevailing method for manufacturing commercially available microfluidic devices comprises generally of the following sequence of steps:

1) Spincoating a layer of photoresist on a substrate, typically a piece of flat Pyrex® glass with or without a layer of chrome.

2) Fabricating a photomask with the desired microfluidic design with methods known in the art.

3) Imprinting the desired microfluidic design on the photoresist by exposing the photoresist coating to light through the photomask with the design on it:

4) Develop the photoresist coating so that the locations for microfluidic features on the glass will be bare, and the rest of the glass will be under the coating.

5) Direct etching of the exposed areas with acids such as hydrofluoric acid (HF) so that channels, reservoirs, etc., will be formed by the acid removal of the glass.

However, other methods are available depending upon the type of material that forms the substrates. For example, insulating substrates including polymers have been disclosed as the substrate materials for planar devices. Fox example, U.S. Pat. No. 5,126,022, discloses polymeric substrate materials in particular PMMA because of its optical clarity in the visible wavelengths making it suitable for laser induced fluorescence (LIF) detection. However, dimensions created by injection molding in conventional microfluidic devices has been limited and devices having dimensions less than 100 µm has not been disclosed. There are other disclosures where the injection-molded microfluidic features are distorted.

It is, however, desirable to fabricate microfluidic devices with at least a part of some microfluidic element not completely surrounded by the substrates. In two disclosures, U.S. Pat. No. 6,074,725 and U.S. Pat. No. 6,210,986 channels design with the channels formed by walls situated above the surface of the substrate is described. In both of these disclosures, the channel walls are built originally flat substrates. In U.S. Pat. No. 6,074,725, the walls were built from liquid polymer deposited from a print head drop for drop. The channel built involves two seams or interfaces with the substrate. Since polymer materials suitable for printing may not be suitable for microfluidic application, the seams may create much stress. The drying of polymer from a solution may distort the shape of the wall in an ill-controlled manner.

In U.S. Pat. No. 6,210,986, a microfluidic device with walls deposited on a conducting surface preferably some doped silicon surface using semi-conducting fabrication technology is disclosed. Again the material used for the wall and the substrates is different, and the walls of the channels are "free-standing" on an originally flat surface rather than an integral part of the substrate. It has also been shown numerous times that semiconductor substrates may not be used in applications such as capillary electrophoresis because of the use of high voltages, which cause the semiconductor to breakdown dielectrically.

SUMMARY

A number of different microfluidic devices are provided herein. These devices can be fabricated using insulating substrates such as polymers, glass, silicon compounds, ceramics, or quartz, with polymer substrates being the preferred substrates. The device may also be made with substrates that are only partially planar. This device may also be made with multiple substrates that are bonded together in more than one plane. The preferred manufacturing method is injection molding of polymers. The exemplary microfluidic devices are made of at least two substrates, namely first and second substrates. Additional substrates may be bonded to the first or second substrates. The substrate may contain microfluidic features such as channels as well as structures that accept conventional fittings such as pipe fittings and microtight fitting. The first substrate has channels and other microfluidic features at least partially raised above the nominal surfaces of a locally substantially planar polymer substrates.

The at least partially raised channel is then covered by the second substantially planar substrate with features that may or may not have features designed into the surface of the second substrate to align the corresponding microfluidic features to those in the first substrate. The raised walls of the microfluidic feature, such as a channel, are an integral part of the substrate, i.e., the raised walls are not deposited onto a planar substrate by any means known in the art. The integral raised walls add substantial structural integrity and rigidity to the function of the channel. The raised walls of the channel may be used as a nozzle for electrospray mass spectrometry. The raised walls of the channel also allows the various substrates to self align when corresponding mating structures are fabricated on the mating surfaces of the various substrates. The raised nature and the rigid nature or the channel walls make accessible at least two wall surfaces of the channel that are now available for design features that greatly enhance the utility of the channel. Parts of the raised wall can be made thinner than the rest without substantially affecting the structural integrity of the channel. The thinned parts of the raised wall can be made into optical window for exceptional transmission, or as diaphragm for valves controlling flow of the fluid inside the channel, and facilitates heat exchange between the inside of the raised channel and the outside of the raised channel. With a metal deposited on the thinned part of the wall, the thin wall becomes the diaphragm of an electrostatically activated valve. Likewise the metal and other optical coatings deposited on the outside surface of the wall may create optical mirrors for a variety of optical detection technology.

The inside surface of the raised wall of the channels may also contain structural features that serve as filter, restricted flow, etc.

The raised and structurally rigid nature of the raised walls of the channel also creates space between the first and second substrates after the first and second substrate have been appropriately assembled. This space can be used to position optical fibers, optical waveguide, electrodes for supplying electric field for the electrostatic valve, coolant or forced air for cooling the channel, and other devices for improving the performance of the device. The space also allows the application of adhesive to bond the first and second substrates after the channel is enclosed. The alignment features which typically include precisely fabricated protrusions and their corresponding equally precisely fabricated receptacles or recess to mate with a tolerance better than 25 μm also serve as devices that mechanically and partially secure the two substrates together, making the adhesive or thermal pressure bonding known in the art far more effective. Mechanical pressure such as one exerted by a clamp over the alignment features may be sufficient to secure the two substrates together to form a liquid-tight seal. Once all the elements that are needed to make the microfluidic device work optimally, the space between the two substrate may be at least partially supported with another polymer for higher stability and protection of the raised walls of the microfluidic features. Likewise additional protrusions and/or corresponding recesses can be built into this space to further support of the raised walls as well as further alignment.

This application further discloses channel design architecture that has non-interacting channels and intersecting channels on the same substrates. For the non-intersecting channel design, all the design features and advantages of the non-intersecting channels disclosed in U.S. provisional patent application Ser. No. 60/265,431, which is hereby incorporated by reference, are applicable to the raised channel with integral walls here. The use of the alignment features and the degree or precision of the fit between the protrusion and recessed described in this application do not need to be universally applied to all the microfluidic features in the microfluidic device. For example, only one or two microfluidic features may need alignment features that allow alignment to better than 25 micron tolerance while the rest may have the corresponding features in the two substrates may be aligned to 100 micron tolerance.

This application further discloses a microfluidic device that is assembled from segments of microfluidic features using the built-in alignment features such as the raised walls of the channels or protrusion/recess pairs to comprise of channels, nozzles, optical detectors, distillation columns, etc. to form a device of specific applications such as an electrospray-mass spectrometer interface. The invention further comprises segments of standard dimensions with standard alignment features so that the user may assemble microfluidic devices of specific applications using standard prefabricated segments.

This application further discloses inventions that comprise design features and method of fabrication of the mold for injection-molding the polymeric microfluidic devices described in this application.

BRIEF DESCRIPTION OF THE FIGURES

All the drawings are schematic drawings not drawn to scale. They are drawn to show the salient features of the inventions described in this application.

FIG. 14 is a top view of a microfluidic device having a set of open nested channels defined by a central channel and adjacent channels;

FIG. 15 is a side elevational view of the device of FIG. 14;

FIG. 16 is a cross-sectional view taken along the line 16—16 of FIG. 14;

DETAILED DESCRIPTION OF PREFERRED EMBODIMENTS

Figure 1:
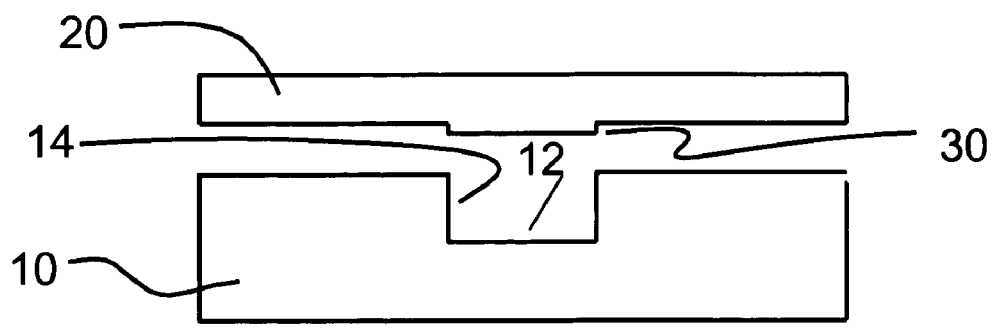
FIG. 1 is a cross-sectional view of a microfluidic device having a microfluidic element, such as a channel.
Figure 2:
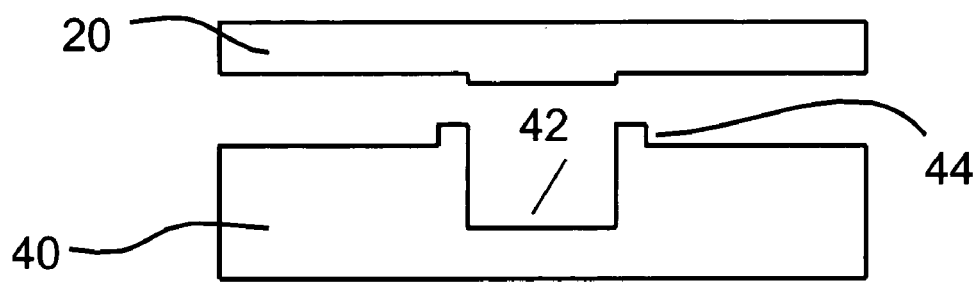
FIG. 2 is cross-sectional view of a microfluidic device having a microfluidic element that is partially defined by raised walls.
Figure 3:
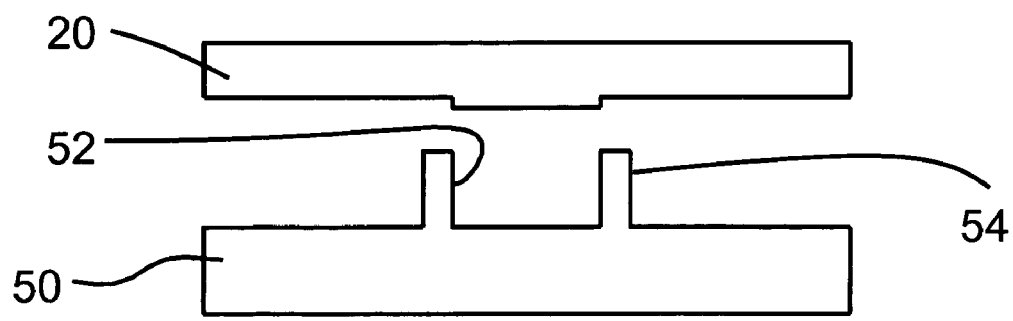
FIG. 3 is a cross-sectional view of a microfluidic device having a microfluidic element that is partially defined by raised walls that form an integral part of the substrate.

Sectional views of various microfluidic devices are shown in FIGS. 1–3 that illustrate some of the features provided the function to form a substrate-to-cover interface. In FIG. 1, a substrate 10 is provided and includes a channel 12 that has a sidewall 14. A cover piece 20 for mating with substrate 10 has a protrusion 30 that extends from the cover piece 20 to fit into the channel 12. The orientation of the channel 12 and the protrusion 30 are designed so that the interface between the channel 12 and the protrusion 30 serve to align and secure the substrate 10 and cover piece 20 connection. The shape of the channel 12 may vary in accordance with the invention and is not necessarily rectangular as shown. Preferably, the protrusion 30 fits into the channel 12 in the substrate 10 with a tolerance of better than 25 µm and the microfluidic channels may be about 20 µm to several hundred µm wide or so in width or diameter.

A cover and substrate can interface to form additional microfluidic features at the interface when raised or partially raised channel walls are used in forming the devices. In FIG. 2, a substrate 40 is provided and includes a microfluidic channel 42 that has partially raised walls 44. Similarly, a substrate 50 with a microfluidic channel 52 with raised walls 54 is shown in FIG. 3. In each embodiment, the raised channel walls are an integral part of the substrate, and are formed of a similar material as the substrate.

In the raised channel embodiment of the invention, the channel bottom may be coplanar with the top surface of the substrate, and the channel sidewalls rise from the substrate surface at an angle between about 45 and 135 degrees. The substrate and the sidewalls are preferably composed of a polymeric material. The polymeric material may be a low melt viscosity polymer.

Additionally, the protrusions may facilitate an interface between multiple substrates containing microfluidic features. The interface may include a recess region to receive protrusions from another substrate so that the channel in one substrate and the microfluidic features such as inlet and outlet access ports for the channel in a second substrate are aligned to an accuracy better than 25 micron.

Figure 4:
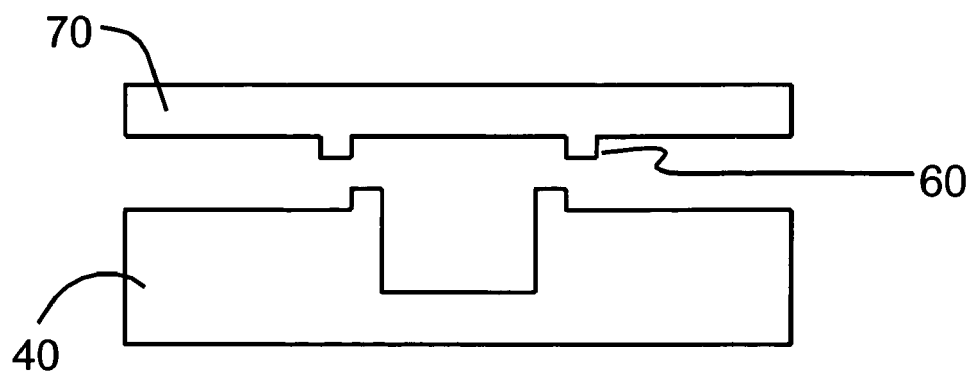
FIG. 4 is a cross-sectional view of a microfluidic device having an alignment structure to align features of one substrate to features formed in another substrate.
Figure 5:
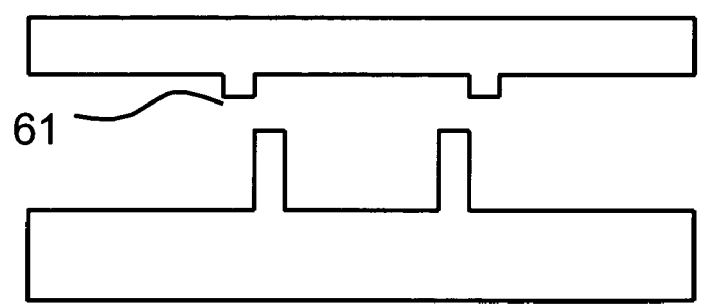
FIG. 5 is cross-sectional view of another microfluidic device having an alignment structure to align features of one substrate to features formed in another substrate.

Similarly to a substrate to cover interface, a substrate to substrate interface may include alignment features incorporated into the channel designs. Such features include ridges rising above the walls of the microfluidic channel, as shown in FIG. 4 as an alignment protrusion 60. These types of alignment protrusions preferably extend up to 100 µm above the top surface plane of the substrate, and preferably up to 1000 µm. The corresponding protrusion on the bottom surface of the second substrate 70, the dimensions of the said protrusion is such that it fits tightly into the channel opening of the first substrate 40. The channel depth with the second substrate 70 in place may be between 10 and 100 µm, and preferably between 10 to 50 µm. This alignment provides features such as access ports in a second substrate to align with features in the first substrate. FIG. 5 illustrates another embodiment in which the substrate 50 of FIG. 3 is mated with a second substrate 59 that has an alignment protrusion 61 extending therefrom. The dimensions of the protrusion 61 are such that the raised walls 54 are disposed between the protrusions 61.

In a microfluidic device comprising more than one channel and other microfluidic features such as reservoirs on the surface of a first substrate, at least one of these microfluidic features may have mating features in the surface of a second substrate to achieve alignment for all the microfluidic features.

Channels with alignment features may also be formed above the top surface of the substrate, i.e., the channel floor is coplanar or above the top surface of the substrate. The alignment features for these raised channels may be the same as those described above.

One embodiment of the invention includes channels with variable depths. This may be employed, for example, to increase the optical detection signal by increasing the optical path length through a channel. A channel may increase in depth to increase the optical path length of the optical beam. The floor of the channel may be lowered to achieve greater depth for a specified portion of the channel. To achieve this, effect, the heights of the raised walls of the various microfluidic elements may be adjusted so that when a second substrate is aligned with the first substrate, the microfluidic channels and, other features are properly enclosed.

Figure 6:
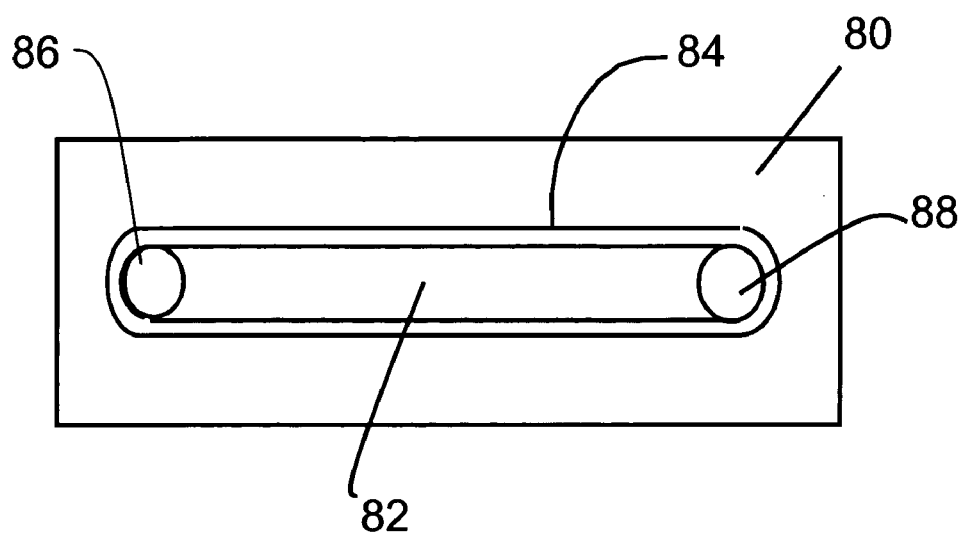
FIG. 6 is a top plan view of a substrate according to one exemplary embodiment containing microfluidic features.
Figure 7:
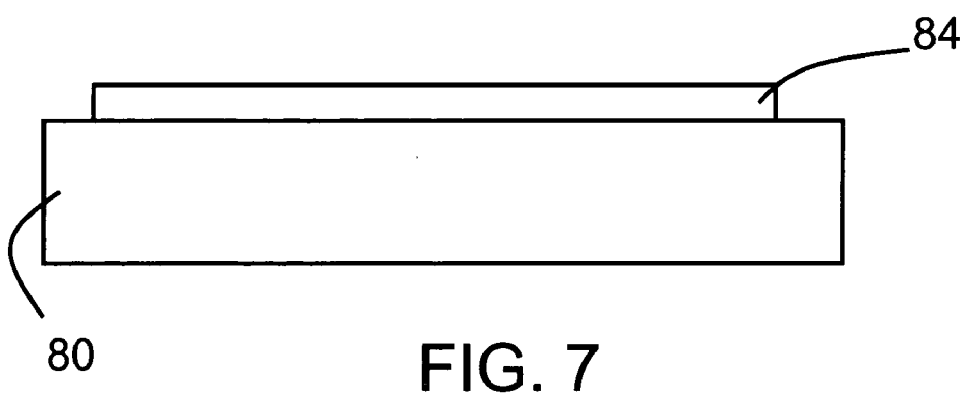
FIG. 7 is side elevational view of the substrate of FIG. 6 illustrating the raised walls that partially define a channel.

Microfluidic devices with a variety of protrusions and raised wall features are illustrated in FIGS. 6–13. FIG. 6 provides a top view of a substrate 80 containing a microfluidic channel 82 with raised walls 84. The device includes one fluid inlet port 86 and one fluid outlet port 88. A side view of this device is shown in FIG. 7 to illustrate the elevation of the raised channel walls 84.

In general, the thickness of a raised channel wall may be about 25 μm, and preferably larger than 100 μm, or may be of more than one thickness.

Along the length of the raised wall, a small portion of the wall, about 1 mm or longer, may be made thinner than the rest of the wall thickness, e.g. less than 25 micron. On the opposite side of the thinned region of the raised wall channel, a corresponding portion of the channel wall may likewise be thinned out. The thin regions of the wall may provide diaphragms for a flow-control valve. Dimensions of the thinned regions on the wall are determined according to the elastic properties of the polymer forming the device. The thinned region of the wall allows enough flexing so that non-elastomers may be used as diaphragms. To actuate the thinned walls, a metal film may be deposited on the outside surface of the each thinned wall. When a high voltage difference is applied across the metal films through the width of the channel, electrostatic attraction of the two electrodes through the dielectric (the polymeric walls) will flex the thinned polymeric wall so that the channel size can be restricted to control flow. By varying an applied voltage, the thin wall diaphragm may be used to create pumping action for the fluid inside the channel. A set of thin-wall diaphragm valves with their respective electrodes for supplying voltages appropriately located in a set of intersecting channels may be used to direct the flow of the fluid from one channel to another.

The actuation of the thinned wall as diaphragm may be achieved through pressure means. Pneumatic pressure may be applied by a high gas pressure outside of the raised channel wall. The higher pressure outside the channel may flex the thinned walls toward each other. For pneumatic activation, only one thinned wall may be needed if one thinned wall can flex enough to close the channel. Another pressure means may be mechanical pressure exerted by a plunger or piston-like structures, or any structures that serve the purpose of exerting pressure on the thinned part of the wall or walls. The mechanical pressure generator does not need to be an integral part of the microfluidic devices.

The thinned walls of the channel may also be located in the first substrate such that the one portion of channel bottom, and the corresponding portion of the cover of the channel are thinned to form the diaphragms.

Figure 8:
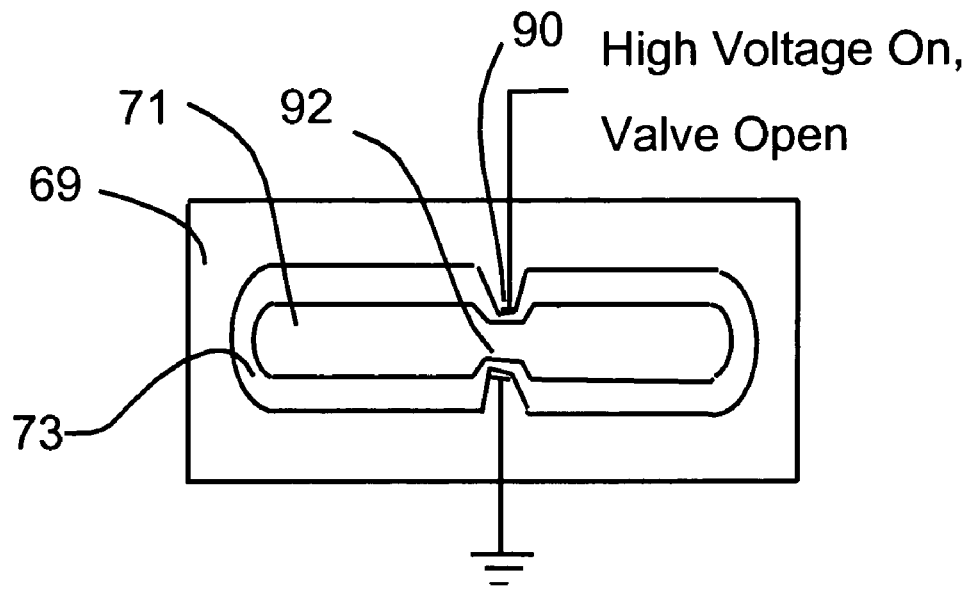
FIG. 8 is a top plan view of a microfluidic device having a microfluidic channel with a diaphragm built into each side of the raised channel wall.
Figure 9:
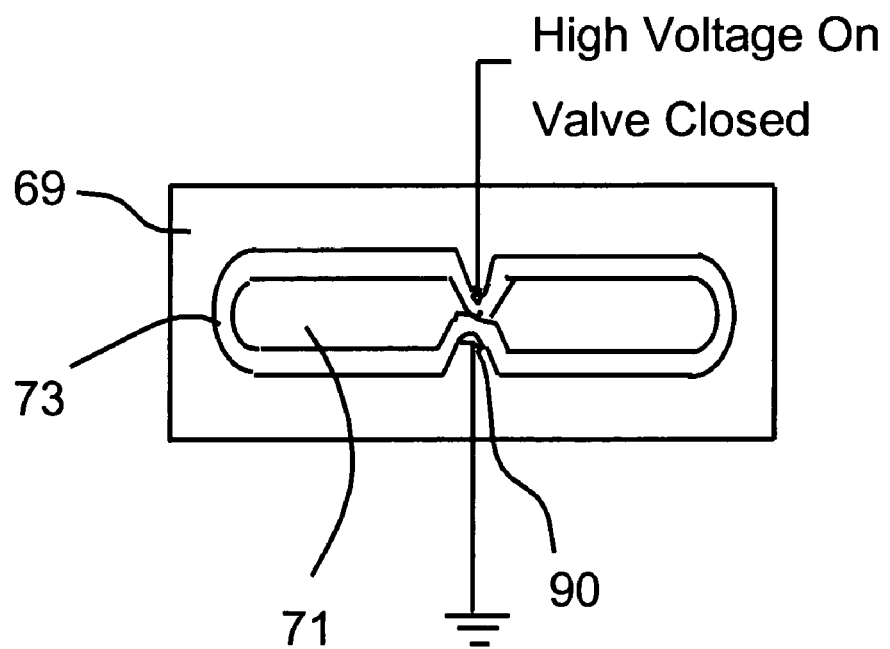
FIG. 9 is a top plan view of the device of FIG. 8 after a voltage has been applied causing the diaphragms to constrict due to electrostatic forces, thereby closing a valve.

FIG. 8 shows a top view of a microfluidic device 69 having a microchannel 71 without a cover that has a diaphragm 90 formed into opposite sides of the raised channel walls 73. Electrodes 92 are attached to the thin regions of the channel walls that define the diaphragms. The configuration shown in 8 represents an open diaphragm, and a closed diaphragm 90 is represented in FIG. 9. In one embodiment; the opening and closing of the diaphragm is controlled by voltage applied to the electrodes 92. For example, with the voltage turned off, the diaphragm remains open, as in FIG. 8. When the voltage is turned on, the diaphragms are pushed in by electrostatic forces and close the valve, as shown in FIG. 9.

In another embodiment of the invention, both the outside and inside surfaces of the raised walls of the channels may have structural features for special applications. The outside raised wall of the channel may be "fluted" so that a thin region along the wall facilitates heat exchange between the contents of the channel and the medium outside of the channel. In some applications, a plurality of thin regions along the wall may be desired. In these embodiments, the overall strength of the raised channel walls is not substantially affected, as regions of the wall are appreciably thicker. Other types of patterns are also possible. For alignment purposes, the top part of the raised wall preferably is relatively smooth.

Figure 10:
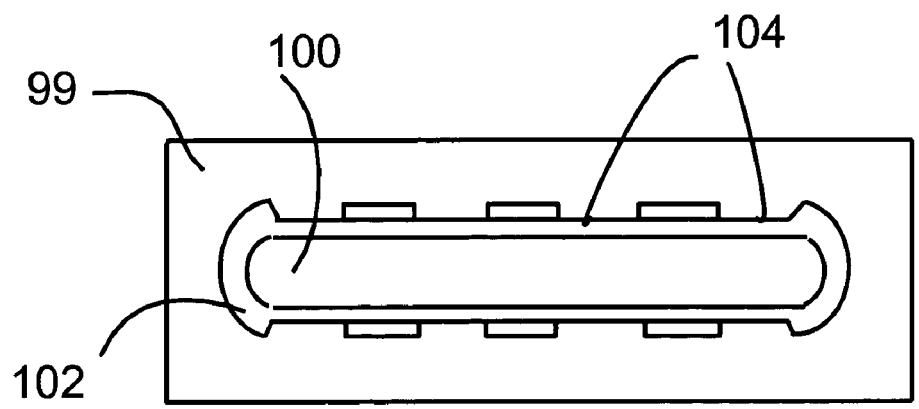
FIG. 10 is a top plan view of a microfluidic device illustrating an open channel defined in part by raised channel walls, wherein the outside surface of the channel walls is sculptured to contain a series of thinned sections to facilitate cooling, pumping, etc.
Figure 11:
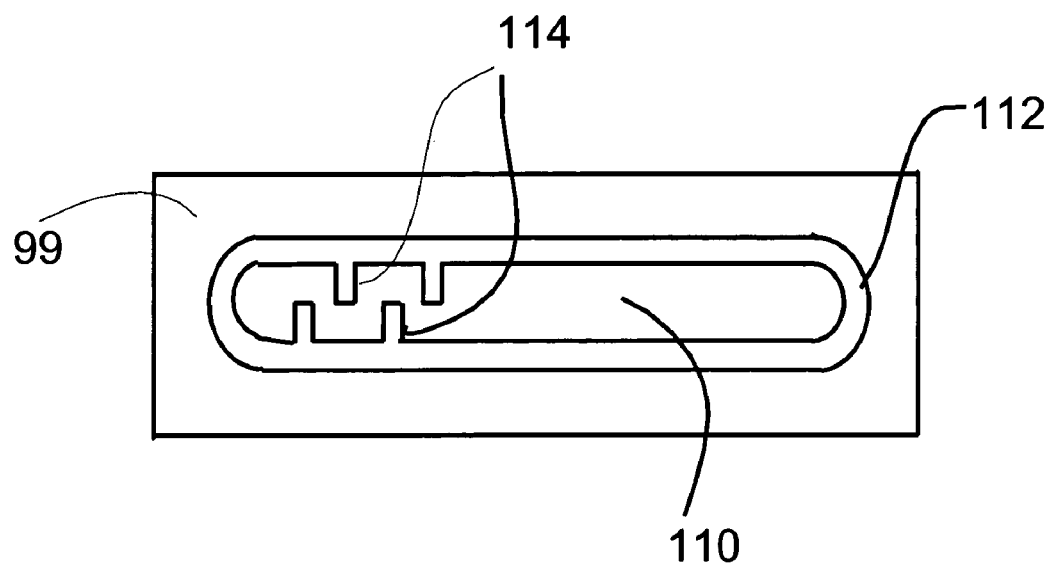
FIG. 11 is a top plan view of a microfluidic device illustrating an open channel defined in part by channel walls having structures that allow the section of the channel to act as a filter or distillation plates for a column.

FIGS. 10 and 11 illustrate the top views of microfluidic devices with raised walls on their surfaces. The inside or outside surface of the raised channel wall may be patterned at least along some length of the wall to provide restricted flow, filtering or other performance features. Generally, a channel incorporating filter or distillation column structures will comprise a channel structure positioned within the channel and oriented perpendicular to the channel sidewall, and perpendicular to the channel bottom.

FIG. 10 shows a microfluidic device 99 having an open channel 100 with raised channel walls 102 in which the outside surface of the raised channel wall 102 contains a series of thin regions 104. These thin regions of the channel walls 102 facilitate cooling, heating or fluid pumping. The top of the raised channel wall 102 may or may not be sculptured to serve as an alignment feature. A schematic view of an open channel 110 with channel walls 112 comprising filter structures 114 is illustrated in FIG. 11. The filter structures 114 allow the section of the channel to act as a filter or distillation plates for a column. Such structures may also be fabricated from the bottom of the channel and the surface of a second substrate that interfaces and aligns with the first substrate. A combination of different patterns on the inside and outside surfaces of the raised walls, the floor of the channel, and the cover side of the channel is possible.

Figure 12:
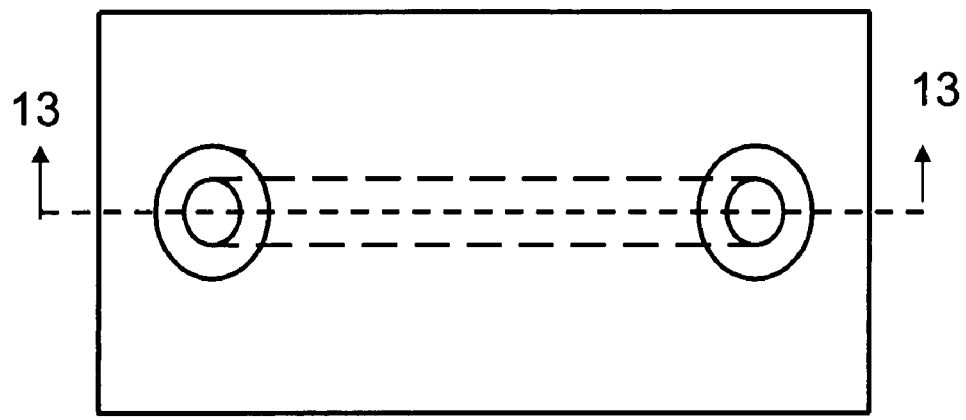
FIG. 12 is a top plan view of a microfluidic assembly having a microfluidic device including a single raised channel and capillaries attached to the inlet and outlet ports to facilitate sample and buffer input from external reservoirs, optical or mass spectrometer detection.
Figure 13:
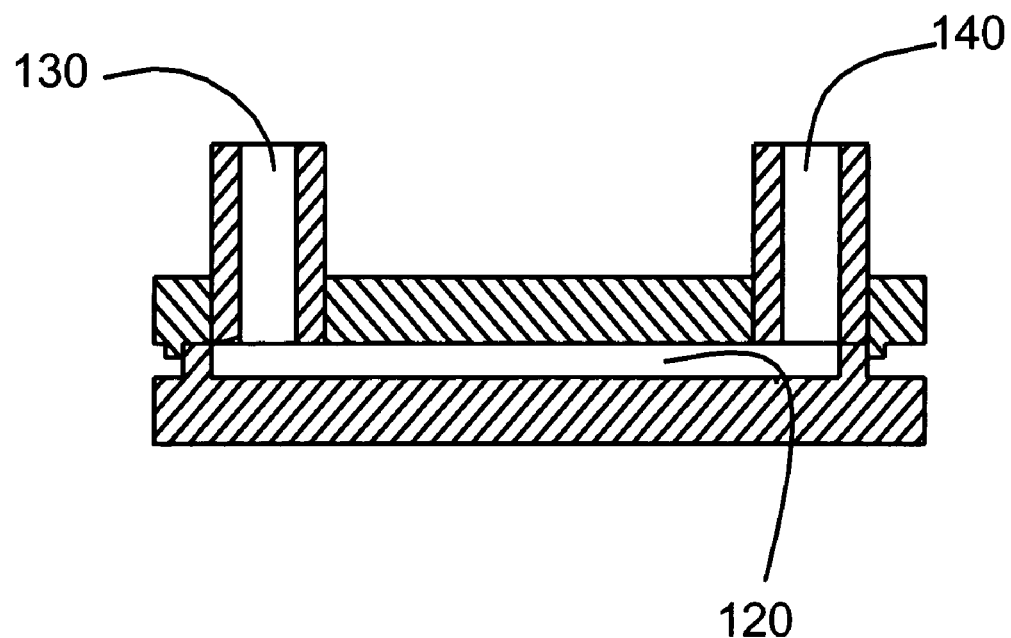
FIG. 13 is a cross-sectional view taken along the line 13—13 of FIG. 12.

FIGS. 12 and 13 provide top and sectional views of an assembled microfluidic device with a single raised channel 120 with capillaries 130 and 140 attached to channel access ports which provide access to the channel for sample and buffer input or transport to a spectrometer for analysis.

FIGS. 14–16 shows the top view of a set of open nested channels. A central channel 150 is a channel that is open at either end that allows fluid inlet and outlet from the two sides of the substrate. The channel end openings 152 are shown at the sides of the device substrate. The adjacent channels 154 have a fluid input port 156 and a fluid outlet port 156 that opens on to the side of the substrate in each of the channels 154. The two sidewalls 153 of the central channel 150 are shared by channels 154 on each side. The sectional view of FIG. 16 shows a substrate cutout 160 on the opposite side of the substrate from the channel structures. The substrate cutout 160 can be mated and aligned with another substrate that will provide fluid for channels 154. These nested channels may be used for transporting liquid in the central channel 150 and a gas in the side channels 154. When a nozzle is attached to one end of the channel 150, these nested channels may be used for generating an electrospray.

Figure 17:
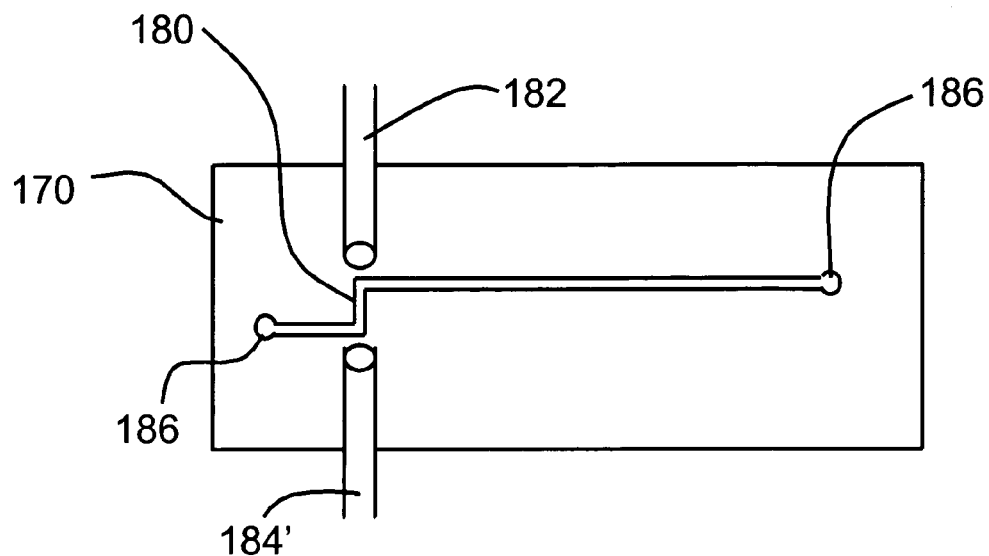
FIG. 17 is a top plan view of a microfluidic device having a raised channel without a cover, where the channel has a "zigzag" feature to increase optical path.
Figure 18:
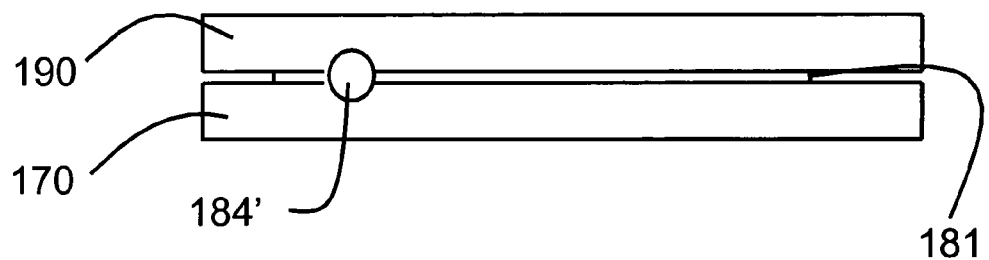
FIG. 18 is a side elevational view of the microfluidic device of FIG. 17 illustrating the zigzag channel and an optical fiber cable that fits in a space between the two substrates.

Another embodiment of the present invention provides for samples detection within the microfluidic device. FIGS. 17 and 18 provide top and side views respectively of a raised channel incorporating an architectural element to provide an extended optical path length for sample analysis. FIG. 17 shows the device without a cover piece or a secondary substrate over a primary substrate 170. A zigzag element 180 in the channel serves to increase the optical path of the sample. The channel is partially defined by raised channel walls 181. Optical fiber cables 182, 184 carry the light from the light source and to the detector-after it has passed through the channel in the zigzag portion 180. Fluid inlet and outlet ports 186 are also shown on this device. The side view of this microfluidic device with a cover piece 190 is shown in FIG. 18. The zigzag element of the channel is obscured in this view by an optical fiber cable 184 that fits in a space defined between the substrate 170 and the cover piece 190. To form the zigzag portion, the channel comprises a first and second linear sections. These linear sections are perpendicular. The channel may also extend into a third linear section, which is nonparallel to the second linear section.

Process of Making Microfluidic Devices

The microfluidic devices of the invention are particularly suited to inexpensive fabrication methods. The devices of this invention may be manufactured by injection molding a suitable thermoplastic. Suitable thermoplastics include polycyclic olefin polyethylene co-polymers, poly methyl methacrylate (PMMA), polycarbonate, polyalkanes, polybutylterephthalate (PBT), polyethylterephthalate (PET), polyalkylketones and polystyrenes. Polycyclic olefin polyethylene co-polymers are especially suitable. Various grades of such polymers by the trade name of Topas® are examples of this type of polymers. Generally thermoplastic polymers with low melt viscosity including thermoplastics blended with liquid crystalline polymers as processing aid and other liquid crystalline polymer containing polymers such as Zenite® (DuPont Company) and the like, high chemical purity, high chemical resistivity and thermal stability are suitable, including non-commercial polymers. Materials with appropriate optical properties are preferred.

The microfluidic devices can be fabricated in accordance with the invention by compression molding and casting on a wide range of polymers. Polymers preferred for microfluidic devices are low melt viscosity polymers with minimal amount of leachable additives. Polycyclic olefin polyethylene co-polymers are preferred. PMMA, polycarbonate, PBT, PET, polystyrenes, polyalcohols such as polybutanol and polycrylate-polyalcohol co-polymers, ionomers such as Surlyn® and bynel®, and others are suitable Where optical transparency of the substrates is not required, polyalkanes such as polyethylene and polypropylene of different grades, thermoplastics containing liquid crystalline polymers and polymer blends exemplified by commercial products such as Zenite® and the like, fluoropolymers of different grades and different fluorine content may be used. More than one kind of polymer may be used as a substrate in the devices described herein.

A process of making microfluidic devices through injection molding includes first preparing an injection molding mold or mold insert. The injection molding mold or mold insert is typically formed as a negative impression of whatever channel architecture, or device features are desired in the microfluidic device. A polymeric material is injected into the injection molding mold or mold insert, and the polymeric material is cured to form the device component.

Because the channel architecture of the devices described herein provide for interconnecting ducts or capillaries to provide fluids to various channels in multiple layers of substrates, larger critical dimensions are feasible for operation. These larger critical dimensions facilitate alignment between multiple substrates and components, as well permit fabrication by injection molding techniques.

When preparing a microfluidic device by injection molding, a polymeric material is injected into an injection molding mold or mold insert and the polymeric material is cured in the model to form the substrate of the microfluidic device and the substrate is removed from the injection molding mold or mold insert.

An injection molding mold or mold insert may be prepared from materials such as metal, silicon, ceramic, glass, quartz, sapphire and polymeric materials, and forming the negative impression of the channel architecture may be achieved by techniques such as photolithographic etching, stereolithographic etching, chemical etching, reactive ion etching, laser machining, rapid prototyping, ink-jet printing and electroformation. With electroformation, the injection molding mold or mold insert is formed as the negative impression of the channel architecture by electroforming metal, and the metal mold is polished, preferably polished to a mirror finish.

For non-metallic molds for injection molding, the mold may be made of a flat and hard material such as Si wafers, glass wafers, quartz or sapphire. The microfluidic design features can be formed in the mold through photolithography, chemical etching, reactive ion etching or laser machining commonly used in microfabrication facilities. Some ceramics may also be used.

Molds may also be made from a "rapid prototyping" technique involving conventional ink jet printing of the design, or direct lithography of resists such as Su-8, or direct fabrication of the mold with photopolymers using stereolithography, direct 3-dimensional fabrication using polymers and other similar and related techniques using a variety of materials with polymers. A resulting polymer-based mold may be electroformed to obtain a metallic negative replica of the polymer-based mold. Metallic molds are appropriate for injection-molding polymers that require the mold to be heated. The commonly used metal for electroforming is nickel, although other metals may also be used. The metallic electroformed mold is preferably polished to a high degree of finish, or "mirror" finish before use as the mold for injection mold. This finish is, comparable to the finish obtained with mechanical polishing of submicron to micron size abrasives. Electropolishing and other forms of polishing may also be used to obtain the same degree of finish. Additionally, the metallic mold surfaces should preferably be as flat and as parallel as the Si, glass, quartz, or sapphire wafers.

For microfluidic features that are larger than 20 µm, chemical etching by photolithography techniques, electric discharge machining (EDM), conventional machining on metal using precision tools, or a combination of both technologies may also be used to fabricate the mold. For microfluidic feature fabrication using chemical etching, a suitable metal is chrome. The resulting machined mold preferably shows a high degree of surface finish, as described herein, and the flatness of the nominal surface of the mold (excluding the microfluidic design features) is at least 25 µm over the surface.

A mold created as described above may be used to injection mold polymers with sub-micron accuracy of micrometer-scale features with width to depth aspect ratio about 2:1 or higher. The width of the feature may be 20 µm or smaller. The temperatures and pressures needed to create these fine microscale structures may deviate substantially from what are typically used for general injection molding.

Generally, the injection molding molds or mold inserts reflect the negative impression of the channel architecture and features for the desired microfluidic device. The negative impression of the channel architecture and features, preferably have a width greater than 100 µm and a height between 10 µm and 50 µm.

Ink-jet technology may be applied in fabricating the microfluidic devices directly, or in fabricating the molds used making microfluidic devices by injection molding. Ink-jet printing technology provides the desired microfluidic features to be printed directly on a substrate such as glass, ceramics, silicon, polymers or any organic, inorganic or hybrid materials that form a flat surface for the printing of features. A negative of the microfluidic features may be made by conventional electroplating with copper or, nickel, or any other metals over the device made via printing technology. The materials forming the microfluidic features may be organic, inorganic, or a blend of organic and inorganic materials. After electroplating, the substrate and the printed microfluidic features are separated from the metal mold. The resulting metal mold is suitable for injection molding, compression molding, room temperature embossing and hot embossing. The resulting mold may also be used for castable polymers known in the art.

If only low temperature casting is needed, then the negative of the desired microfluidic features are printed with the ink-jet printer directly on a flat substrate as described above. The resulting device can be used as a mold or master for replicating the devices made of polymers.

Polymers suitable for injection molding include Topas®, a polyethene-polycyclic olefin co-polymer sold by Ticona, polymethylmethacrylate (PMMA), polycarbonate, polyalkanes, PET<PBT, PEEK, polystyrene, and polyacrylate polybutanol co-polymers, thermoplastic blend with liquid crystalline polymer added as processing aid, polyionomers such as Surlyn® and Bynel®.

A master device can be used to make replicas through compression molding with the above polymers and also Teflon AF®. The mold surfaces of the master device preferably have a mirror finish. A master can also be used for casting polymer devices with any polymers that can be polymerized inside the mold with polymer precursors and a catalyst. Polymers suitable for casting with a master are PMMA, polymethylbutyllactone, PDMS and its derivatives, polyurethane, polyalcohols, and other castable polymers.

The following Example is for purpose of illustration only and are not limiting of the present devices.

EXAMPLE 1

Figure 19:
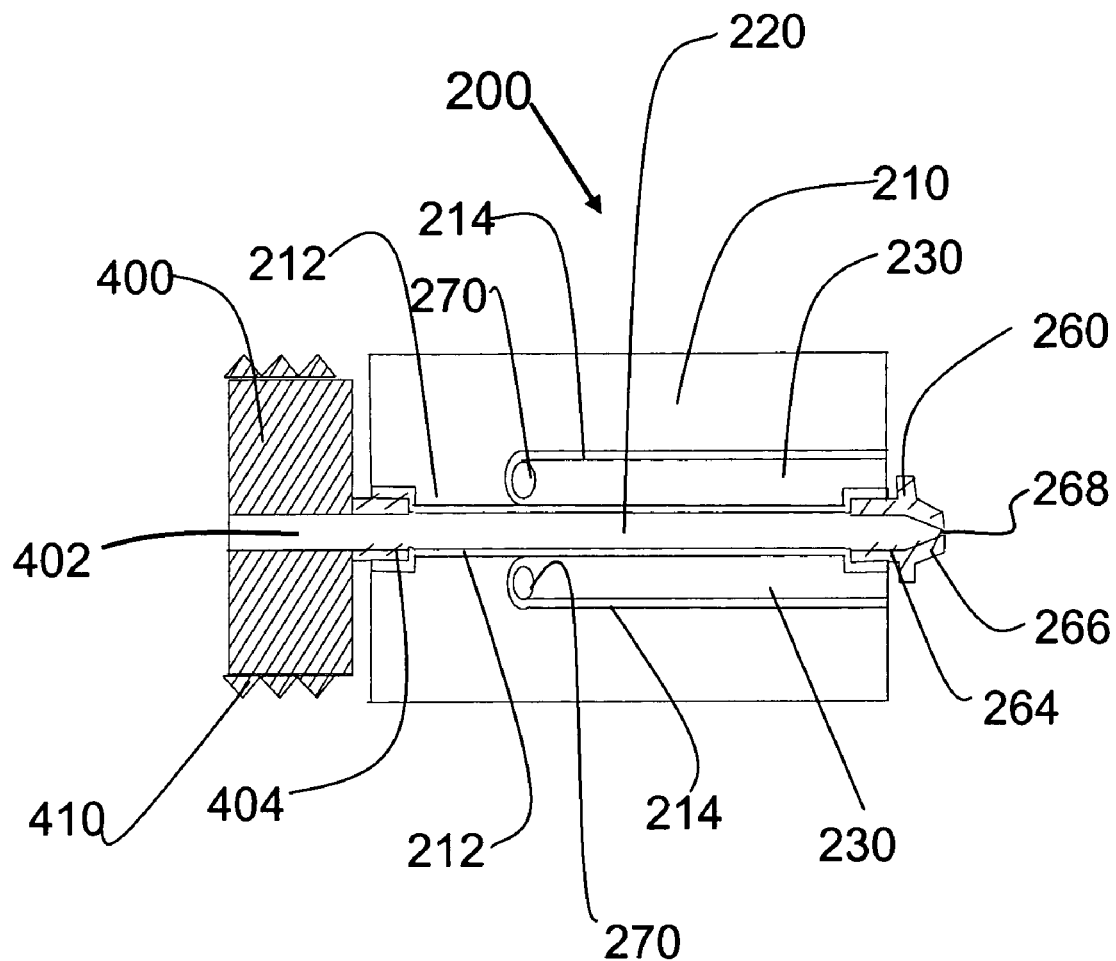
FIG. 19 is cross-sectional top plan view of a microfluidic device assembled with other components to form an electrospray-mass spectrometer interface.
Figure 21:
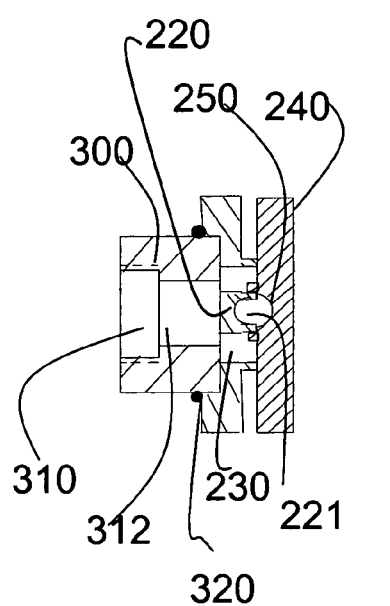
FIG. 21 is cross-sectional view taken along the line 21—21 of FIG. 20.
Figure 20:
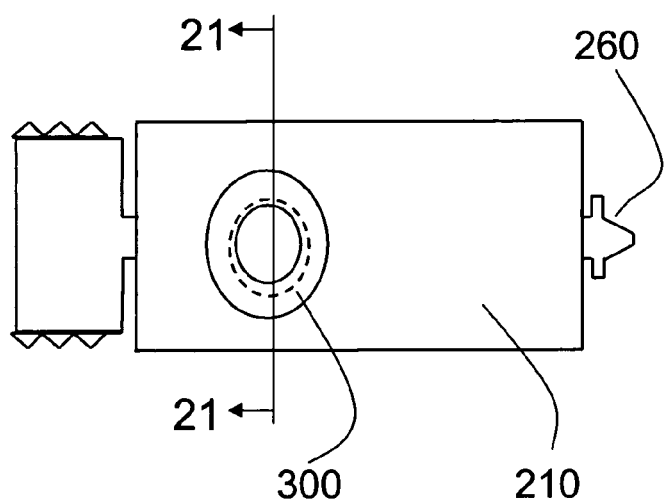
FIG. 20 is a top plan view of the assembly of FIG. 19.

FIGS. 19–21 illustrate yet another embodiment of an exemplary microfluidic device, generally indicated at 200, serving the function of an electrospray-mass spectrometer interface is fabricated using the technology disclosed in this application. The various components of the device 200 are fabricated by injection molding 5 different substrates using a polycyclic olefin copolymer as the substrates. Each of the substrates is aligned accurately with its counterparts with the registration features which may be the raised channel walls, steps in the cover substrate fitting into channel and other locating mechanisms described in this application. The substrates are bonded together with an appropriate adhesive outside of the raised walls of the channel or by heating the substrates to the heat deflection temperature of the polymer and apply gentle pressure of no more than a few hundred psi, or by using a film of hexane on the outside of the channel wall as a solvent to dissolve enough polymer for bonding.

FIGS. 19–21 illustrate one exemplary device 200 and includes a first substrate 210 which may be represented by the substrate shown in FIGS. 14–16, has three parallel and adjacent channels. Each channel formed in the first substrate 210 is formed by raised walls 212 and 214. The raised walls 212 of a middle channel 220 are shared by the middle channel 220 and adjacent channels 230 that are formed on either side of the middle channel 220. The raised walls 212 are 75 μm thick each and 50 μm high.

Referring to FIG. 21 which shows a cross-section of the assembled device with the first substrate 210 and a second substrate 240 in their appropriate positions, the middle channel 220 has a generally hemispherical cross-section (generally indicated at 221) according to this exemplary embodiment and the diameter of the middle channel 220 after the first and second substrates 210 and 240 have been assembled is 90 μm. The middle channel 220 runs the entire length of the first substrate 210. The two adjacent channels 230 are each about 300 μm wide. One end of each of these two channels 230 opens at one end of the first and second substrates 210, 240, while the other end of each of these two channels 230, 240 end about two-thirds of the length of the two substrates 210, 240. The second substrate 240 has a channel 250 that is aligned with the middle channel 220 in substrate 210 to 25 μm tolerance to create a channel with a symmetrical cross-sectional shape.

A third substrate 260 is provided and has a base section 262 that is generally annular in shape. The third substrate 260 has a channel 264 formed therethrough. The third substrate 260 is mated and aligned with one end of the middle microfluidic channel 220 formed by first and second substrates 210 and 240. A circular surface 266 serves as the nozzle for electrospray mass spectrometry and is metallized by a film of platinum deposited on the outside wall. A nozzle opening 268 has a 20 μm internal diameter, and 100 μm outer diameter according to one embodiment. In each of the 300 μm wide channels 230 on substrate 210, a port 270 of about 300 μm in diameter is located and in fluid communication with the 300 μm wide channel 230. The port 270 opens into a circular depression on the opposite side of substrate 210 so that the depth of the port 270 from the depression to the fluid channel 230 is about 500 μm.

Into this circular depression is mated a circular substrate 300 to fit to within 25 μm of the circular opening. Adhesive can be used on the outside of the circular opening to provide for coupling between the two components. On the opposite side of this circular protrusion is an opening 310 with pipe threads or microtight threads. A channel 312 up to 2 mm in diameter runs from the side of the opening 310 with the threads to the center of the other side of substrate 300. An external gas source such as dry nitrogen gas may be connected to the pipe or microtight fitting to supply gases for nebulizing the liquid coming out of the nozzle end of the middle microfluidic channel 220. A liquid used as a sheath liquid may also be supplied instead. If both are needed, an additional set of two channels placed adjacent to the 300 μm channels may be fabricated. Likewise if the adjacent channels 230 are not needed, they do not need to be present on substrate 210 (and thus only the middle channel 220 is present).

The end of the middle channel 220 opposite to the nozzle end is mated and aligned with raised channel walls 404 of a channel 402 formed in a third substrate 400 which also has a microtight fitting receptacle 410 for accepting a capillary that comes from the sample outlet of a HPLC, a capillary electrophoresis machine or another sample injection source such as a microtiter plate. Substrate 400 may also be a microfluidic device performing a variety of functions such as separation, dilution, concentration, etc and substrate 400 in this case may be made of two parts. Substrate 300 may be fabricated by conventional mechanical machining. After the assembly of each two substrates, a UV curable adhesive 320 may be placed between the space made by the raised channels around the outside edges of the bonded substrates and UV cured for added bonding of the substrates. Electrospray is achieved by subjecting the nozzle where liquid and analytes emerge to a high electric field. The microfluidic device in this example provides a low cost, disposable electrospray interface capable of nanospray. This device can be fabricated to accommodate more than one sample input in order to multiplex several separation instruments to a single mass spectrometer. It is also understood by one skilled in the art that the middle channel 220 that is mated with the nozzle substrates 260 and 400 may be a channel that performs operations such as liquid chromatography, electrophoresis and the like, and may not have adjacent channels 230 next to it.

Thus, FIGS. 19–21 illustrate an embodiment where several or more substrate are coupled to one another to form a microfluidic assembly, e.g., an interface, and one will appreciate that the present injection molding process that is used to form each of the substrates permits selected substrates to have not only microfluidic features but also to have features that are not microscale in dimension. For example, microchannels, ports and microscale adapter sections can all be formed in a substrate using an injection molding process. By being able to also form features that have larger dimensions (i.e., non microscale) in the same substrate that contains microscale features, the substrate can be coupled to conventional equipment. For example, a capillary tube or gas nebulizer having conventional fittings can be received in the substrate due to the substrate having structures that accept the conventional fittings, which can be in the form of pipe fittings and microtight fittings.

It will be appreciated that the various substrates can be combined in a number of different manners than the aforementioned Example 1 depending upon the precise configurations of the substrates and also the desired application for the microfluidic device. Thus, instead of serving as an electrospray mass spectrometer interface, the combined substrates can receive capillary from conventional separation equipment, with one of the substrates serving as an adapter between the conventional equipment and the main substrate having microscale features formed thereon.

While the invention has been particularly shown and described with reference to preferred embodiments thereof, it will be understood by those skilled in the art that various changes in form and details can be made without departing from the spirit and scope of the invention.

What is claimed is:

1. A microfluidic combination comprising:
   a first substrate comprising a top surface with a first microchannel having a bottom formed thereon, wherein the first microchannel is disposed in between a first structure comprising a first pair of upstanding walls that protrude outwardly from the top surface, the bottom of the first microchannel being coplanar with the top surface, and wherein the first substrate and the first pair of upstanding walls are formed as an integral, unitary structure formed of the same material;
   a second substrate having an integral second structure that protrudes outwardly from the bottom surface thereof, wherein the second substrate and the second structure are formed of the same material;
   one of the two structures being adapted to be received in between the other structure so as to produce a frictional fit therebetween resulting in a sealed microchannel being defined between the two substrates.

2. The microfluidic combination of claim 1, wherein the second substrate is connected to a capillary tube.

3. The microfluidic combination of claim 1, wherein the sealed microchannel is open at one edge of the substrates.

4. The microfluidic combination of claim 1, further including a third substrate having a third microchannel formed therethrough from one end to the other end, the third substrate being in the form of a nozzle with the one end being a nozzle opening, the third microchannel being in fluid communication with the sealed microchannel.

5. The microfluidic combination of claim 4, wherein the nozzle opening has a diameter of about 20 micron and the one end has a conical shape that terminates at the nozzle opening and has an outer diameter of about 100 micron.

6. The microfluidic combination of claim 1, wherein the sealed microchannel includes a port that opens into a depression formed on a second surface of the first substrate opposite the top surface where the first microchannel is formed.

7. The microfluidic combination of claim 6 further comprising one or more adjacent microchannels that are disposed immediately adjacent to the first microchannel and further including a third substrate that includes an opening that forms an entrance into a third microchannel that extends to an opposite face of the third substrate, the third microchannel being in fluid communication with the one or more adjacent channels but not the first microchannel.

8. The microfluidic combination of claim 7, wherein the opening has microtight threads formed therein for coupling the third substrate to another device.

9. The microfluidic combination of claim 1, wherein the combined first and second substrates comprise an electrospray-mass spectrometer interface.

10. A microfluidic combination of claim 1 wherein the two substrates are injection molded polymeric substrates, the combination further comprising:
    a third injection molded polymeric substrate that includes a third microchannel that is aligned with the sealed microchannel and is coupled to the substrates to permit fluid communication between the third microchannel and the sealed microchannel, the third substrate further having microtight threads for coupling the third substrate to another component.

11. The microfluidic combination of claim 10, wherein the sealed channel extends an entire length of the first and second substrates such that the sealed microchannel is open at both ends.

12. The microfluidic combination of claim 1 further comprising a pair of adjacent microchannels that surround the sealed microchannel, each of the adjacent microchannels being formed on the top surface such that the bottom thereof is coplanar with the top surface, the adjacent microchannels defined by a third pair of upstanding walls that protrude from the top surface.

13. The microfluidic combination of claim 12, wherein the first substrate has a pair of ports formed therein, each port being in fluid communication with one of the adjacent channels.

14. The microfluidic combination of claim 10, further including:
    a nozzle assembly comprising the third substrate, and a fourth substrate that is in fluid communication with the sealed microchannel at the end opposite the end where the third substrate is coupled thereto, the fourth substrate having a nozzle microchannnel formed therethrough that terminates in a nozzle opening.

15. The microfluidic combination of claim 14, wherein the nozzle opening has a diameter of about 20 micron.

16. The microfluidic combination of claim 14, wherein the combined four substrates comprise an electrospray-mass spectrometer interface.

17. The microfluidic combination of claim 1, wherein the second structure comprises an elongated protrusion, the elongated protrusion being received between the first structure.

18. The microfluidic combination of claim 1, wherein the second structure comprises a second pair of upstanding walls so as to define a second microchannel therebetween.

19. The microfluidic combination of claim 1, wherein the first substrate and the second substrate are formed from an injection moldable material.

* * * * *